(12) United States Patent
Tindall et al.

(10) Patent No.: US 8,744,792 B2
(45) Date of Patent: Jun. 3, 2014

(54) MEASUREMENT APPARATUS

(75) Inventors: Ian Francis Tindall, Bournemouth (GB); James Hugh Vincent, Milton Keynes (GB); Linda Phillips Crumpler, Clemmons, NC (US)

(73) Assignee: Molins PLC, Milton Keynes (GB)

( * ) Notice: Subject to any disclaimer, the term of this patent is extended or adjusted under 35 U.S.C. 154(b) by 352 days.

(21) Appl. No.: 12/886,610

(22) Filed: Sep. 21, 2010

(65) Prior Publication Data

US 2011/0231136 A1 Sep. 22, 2011

(30) Foreign Application Priority Data

Sep. 25, 2009 (GB) .................................. 0916908.7

(51) Int. Cl.
*G06F 19/00* (2011.01)
(52) U.S. Cl.
USPC ........................... 702/100; 131/328; 131/280
(58) Field of Classification Search
CPC .................................................. G01F 25/0007
USPC .................................... 702/100; 131/328, 280
See application file for complete search history.

(56) References Cited

U.S. PATENT DOCUMENTS

| 5,734,092 | A | 3/1998 | Wang et al. | |
|---|---|---|---|---|
| 6,237,760 | B1 * | 5/2001 | Parker et al. | 206/273 |
| 2005/0087202 | A1 * | 4/2005 | Norman et al. | 131/280 |
| 2009/0120449 | A1 * | 5/2009 | Tindall | 131/334 |

FOREIGN PATENT DOCUMENTS

| CN | 201014975 | Y | 1/2008 | |
|---|---|---|---|---|
| CN | 101196453 | A | 6/2008 | |
| CN | 201138321 | Y | 10/2008 | |
| GB | 2 370 649 | A | 7/2002 | ............ G01N 15/08 |
| GB | 2 399 422 | A | 9/2004 | ............ G01N 15/08 |
| GB | 2 437 978 | A | 11/2007 | ............ G01N 21/59 |
| JP | 63208739 | A | 8/1988 | ............ G01N 13/00 |

OTHER PUBLICATIONS

Baker et al., "The Diffusion of Carbon Monoxide out of Cigarettes". Beiträge zur Tabakforschung, Band 9, Heft 3, Oct. 1977, pp. 131-140.
Norman et al., "Measurement of Gas Diffusion Capacity of Cigarette Papers", Beiträge zur Tabakforschung International/Contributions to Tobacco Research, vol. 21, No. 8, Dec. 2005, pp. 425-434.
"Paper Diffusivity Meter User Guide", Sodim Instrumentation SAS, pp. 1-67.

(Continued)

*Primary Examiner* — John Breene
*Assistant Examiner* — Haihui Zhang
(74) *Attorney, Agent, or Firm* — Woodard Emhardt Moriarty McNett & Henry LLP

(57) ABSTRACT

A measurement apparatus is disclosed in which a barrier separates a chamber into a first region and a second region. The barrier is of a known thickness, and it comprises holes having a known radius. Gas flow means provide a flow of a carbon dioxide in the first region and a flow of a nitrogen in the second region. A gas detector measures the concentration of carbon dioxide in the second region and a processor calculates the theoretical diffusive flux from one region to another based on the known properties of the through-holes. The processor is arranged to calculate a calibration parameter in order to relate the measured parameter to the theoretical diffusive flux, based on the known properties of the through-holes.

13 Claims, 2 Drawing Sheets

(56) References Cited

OTHER PUBLICATIONS

Drake et al., "On a Cell to Measure Diffusion Coefficients of Gases Through Cigarette Papers", Int. J. Heat Mass Transfer, vol. 23, 1980, pp. 127-134.

Muramatsu, et al., "A Model Study on the Diffusion and the Dilution of Low Molecular Weight Gaseous Components through Cigarette Paper during Smoking", Beiträge zur Tabakforschung, Band 9, Heft 3, Oct. 1977, pp. 141-146.

Durocher, et al., "Diffusion of Gaseous Components through the Wrapper of a Cigarette", Beiträge zur Tabakforschung International, Band 9, Heft 4, Jul. 1978, pp. 201-207.

Chinese Application No. 2010500647.2 Examination Report dated Dec. 23, 2013.

* cited by examiner

MEASUREMENT APPARATUS

CROSS REFERENCES TO RELATED APPLICATIONS

This application claims priority to United Kingdom Patent Application No. GB 0916908.7 filed Sep. 25, 2009 which is expressly incorporated by reference herein, in its entirety.

BACKGROUND OF THE INVENTION

This invention relates to apparatus for measuring the diffusion capacity of a barrier or the diffusive flux through a barrier and a method for calibrating the apparatus.

Cigars, cigarettes, and cigarillos (generally known as smoking articles) typically comprise tobacco cylindrically surrounded by a paper wrapper. In use, a smoking article has a burning coal at one end, and a supply of oxygen is needed to feed the hot coal. Some oxygen is supplied directly to the hot coal from the atmosphere and some oxygen is supplied to the hot coal through the wrapping paper by diffusion. Some combustion products can also leave the region of the hot coal through the wrapping paper.

Cigarette wrapping paper is generally permeable to air by design. There are many known methods for determining paper permeability. These may involve applying a pressure differential across the paper and measuring effects such as gas flow rates that arise by result.

Techniques for determining paper permeability using pressure differential may be effective for determining the gas flow rate across the paper during puffing of a cigarette (where there is also a pressure differential across the paper). These techniques may be less effective for determining the gas flow rate across the paper during the smoulder phase of a cigarette where there is a minimal pressure differential across the paper.

In addition, while techniques for measuring paper permeability using pressure differentials may be sufficiently accurate when the permeability of the cigarette wrapping paper is relatively high, these techniques may lack accuracy in situations where the permeability of the paper is relatively low. One example where this may occur is in the measurement of the permeability of paper used in fire standard compliant smoking articles.

Fire standard compliant smoking articles use wrapping paper with annular bands of different permeability. Extended bands of standard permeability are punctuated by thin bands of low permeability. A burning cigarette may be extinguished when the combustion reaches bands of low permeability because (in the absence of a puffing action) insufficient oxygen may be supplied to the burning coal by diffusion through the wrapping paper.

Other methods for measuring the propensity of gas to be transported across a paper barrier involve measurements of the diffusion capacity of the barrier. Diffusion capacity is analogous to permeability and is measured in the same units. In these methods, a chamber is separated into two regions by a paper barrier, and a pressure differential of zero is applied across the barrier. Different types of gas are provided on either sides of the paper barrier, and gas concentration meters can measure the rate of diffusion through the paper. These methods have the advantage of being representative of behaviours present during smouldering. One apparatus for measuring the diffusion of gas through cigarette wrapping paper is described in US 2005/0087202.

A problem with standard apparatus that measure diffusion capacity, or that measure the diffusive flux of gases across a barrier, is in the verification of the accuracy and stability of the measurements. Known apparatus may be able to determine a difference between the diffusion capacities of different samples, but may lack the ability to provide a reliable absolute measure of diffusion capacity or diffusive flux.

The present invention addresses this problem and aims to provide apparatus and methods for use in calibrating apparatus in the measurement of diffusive flux.

According to an aspect of the present invention there is provided measurement apparatus comprising: a chamber; a barrier separating the chamber into first and second regions, wherein the barrier comprises one or more through-holes each with known properties; a detector arranged to measure a parameter that is related to the diffusive flux of a gas from one region to the other, through the barrier; a processor to connect a parameter derived from the measurement and a parameter derived from the known properties of the through-holes; and data storage means for storing the calibration parameter calculated by the processor, wherein the barrier is replaceable by a further barrier, such that the apparatus is able to determine a parameter that is related to the diffusive flux across the further barrier by measuring a parameter with the detector and applying the calibration parameter stored in the data storage means.

In this way the apparatus can accurately determine the diffusion capacity of a barrier. This may be achieved by measuring a parameter that is related to the diffusive flux of gas from one region to the other, through the barrier, applying the calibration parameter, and calculating the diffusion capacity based on the calibrated measurement. The actual measurement made by the detector may be the concentration of gas that has diffused from one region of the chamber to the other. This measurement is, of course, related to the diffusive flux from one region to the other, through the barrier. In other embodiments the detector could measure other parameters such as gas flow rates through the barrier as these may also be related to the diffusive flux of gas from one region to the other.

Calibration of the apparatus may be important because measurements of diffusion capacity may be inaccurate otherwise. This may be of particular benefit in the manufacture of cigarette papers where fine measurements of the diffusion capacity of paper are required.

In the industry it is common to refer to the diffusivity or the diffusion capacity of a barrier in order to refer to the propensity of the barrier to allow diffusion. The diffusion capacity is often denoted as D* and is measured in units of $ms^{-1}$ which are the same units as are often used to measure permeability.

Preferably the apparatus comprises a calibration coefficient pre-stored in the data storage means for converting a measured parameter into a calibrated parameter related to the diffusive flux of a gas across the barrier. The calibration parameter calculated by the processor may replace this pre-stored calibration coefficient, or it may be used as a corrective factor.

The calibration parameter may connect a variety of different parameters. For example, the processor may be arranged to calculate a parameter that is related to the theoretical diffusive flux through the barrier, based on the known properties of the through-holes, and the calculated calibration parameter may connect the measured parameter and the calculated parameter. Thus, the calibration parameter may connect the actual concentration of gas that is measured at the detector with the theoretical concentration of gas that would be expected. In an alternative the processor may calculate a parameter from the measured parameter that is related to expected properties of the through-holes. In this example the calibration parameter may connect the known properties of the through-holes with the expected properties based on the measurement of the detector.

Preferably said known properties of the through-holes include the depth and area of the through-holes. In this way the theoretical diffusive flux across the barrier may be calculable from first principles according to Fick's laws of diffusion. The theoretical diffusive flux across the barrier may be converted into another parameter such as the theoretical concentration of gas that is expected for detection by the detector.

The known area of each hole may be based on the diameter or the radius of each hole. Thus, the known properties of the through-holes may include the depth and diameter of the through-holes. The through-holes may take any shape, but it may be most convenient to provide a circular shape.

It may be desirable to provide a barrier with a low diffusion capacity when calibrating the apparatus. This may be desirable when the apparatus is intended to be used to measure the diffusive flux across materials such as some cigarette papers, as these are known also to have a low diffusion capacity. A greater accuracy can be achieved by calibrating the apparatus with a barrier having a diffusion capacity that is as similar as possible to the diffusion capacity of those barriers that will subsequently be analysed.

A barrier with a low diffusion capacity may comprise through-holes with a large depth, and/or a small number of through-holes, and/or through-holes with a small area. It may be particularly convenient to provide a barrier with a low diffusion capacity by providing through-holes that have a depth that is greater than the thickness of the barrier. This may be achieved by fixing a tube to the barrier. All of the through-holes in the barrier may be defined at least in part by tubes in this way.

The at least one through-hole with a depth that is greater than the thickness of the barrier may be defined at least in part by a tube that is fixed to the barrier. It may be particularly desirable to define a through-hole with a tube because the tube can be manufactured to have well defined properties. For example, the tube may be a regular cylinder with well defined, smooth openings. In this way, predictable effects may occur when air is drawn through the tube by diffusion. Thus, any errors in the calculated parameter related to the theoretical diffusive flux across the barrier that are due to turbulent airflow in the through-holes may be reduced. The ratio of hole area or circumference to depth may be chosen to ensure diffusive flow with a low pressure drop across the barrier.

The tube may extend from a surface of the barrier, and the tube may be fused or fixed to the barrier. The tube may also extend through the barrier such that it projects from opposing surfaces thereof. Preferably the tube is of glass or ceramic material.

At least one of the through-holes in the barrier may have a depth equal to the thickness of the barrier. In this way, the through-hole may be a simple hole in the material of the barrier. This may be desirable due to ease of manufacture. The through-holes may be drilled in the barrier by any convenient means such as by a laser.

Preferably the barrier is of a material that is substantially impermeable to air in the absence of any through-holes. Thus, any diffusion across the barrier may be due to diffusion through the known through-holes only. The barrier may be made of one of metal, glass, ceramic and polymer material. Preferably the barrier is made of metal foil which may be thin and flat.

The material of the barrier may have a low coefficient of linear expansion. In this way, the properties of the through-holes may be substantially unaffected by small changes in temperature so that the diffusion capacity of the barrier is substantially independent of small changes in temperature. Another desirable property of the material chosen may be its propensity to be drilled with holes using a laser or similar device.

A suitable choice of material for the barrier can allow simple cleaning of the barrier. For example, the barrier may be cleaned by an ultrasonic cleaning bath with a suitable solvent or by heating. Regular cleaning of the barrier may be desirable to avoid any clogging of the through-holes such as may occur through atmospheric contamination. This can avoid any error between a calculated theoretical diffusive flux across a barrier, and an actual diffusive flux which is lower because of clogged through-holes.

Preferably the barrier is clamped when it is held to separate the chamber into first and second regions. The material of the barrier is preferably chosen so that there is no deformation of the barrier due to clamping as such deformation may affect the diffusive flow across the barrier.

Preferably the detector is provided in the first region and the detector is arranged to measure the concentration of a gas in the first region, at least some of the gas having diffused into the first region from the second region, through the barrier. Thus, the concentration of the gas as detected in the first region may be dependent on the rate of diffusion of gases from the first region to the second region.

The diffusivity measurement apparatus may comprise a further detector provided in the second region, arranged to measure the concentration of a gas in the second region at least in part due to the diffusion of the gas from the first region, through the barrier. Thus, the apparatus may be calibrated by measurements from the detector in the first and/or second region. It may be possible for the apparatus to be calibrated based on measurements from one region and for the diffusion capacity of further barriers to be determined according to measurements from the other region.

According to another aspect of the present invention there is provided a method of calibrating measurement apparatus, the method comprising the steps of: separating a chamber into first and second regions with a barrier, wherein the barrier comprises one or more through-holes each with known properties; measuring a parameter that is related to the diffusive flux of gas from one region to the other, through the barrier; calculating a calibration parameter to connect a parameter derived from the measurement and a parameter derived from the known properties of the through-holes; and recording the calibration parameter, such that the apparatus is able to determine a parameter that is related to the diffusive flux across a further barrier by measuring a parameter and applying the recorded calibration parameter.

Preferably the method comprises the further step of calculating a parameter that is related to the theoretical diffusive flux through the barrier, wherein the calculation is based on the known properties of the through-holes, and wherein the calculated calibration parameter connects the calculated parameter and the measured parameter.

Preferably the properties of the one or more through-holes (such as the depths of the through-holes and the area of the through-holes) are known because they have been measured. The measurement of the properties of the one or more through-holes may be undertaken optically or using any other standard techniques so that they are known to a high degree of accuracy.

According to yet another aspect of the present invention there is provided a method of determining a calibrated diffusive flux of gas through paper for a smoking article comprising the steps of calibrating diffusivity measurement apparatus according to the method as previously defined; replacing the barrier with a further barrier to separate the chamber into first and second regions; measuring a parameter that is related to the diffusive flux of gas from one region to the other, through the barrier; and calculating a calibrated diffusive flux at least in part by applying the recorded calibration parameter to the measured parameter.

In this way the diffusive flux across smoking article paper (such as the paper for fire standard compliant cigarettes) can be accurately determined because the measurement apparatus has been properly calibrated. The diffusion capacity of smoking article paper and other related properties may also be determined in this way.

The chamber of the apparatus may include means for active management of the pressure differential across the barrier in order to maintain a minimal pressure differential. The pressure differential is preferably maintained at a level that is low enough so that the diffusive flux is greater that the pressure drive flow. Ideally the ratio of diffusive flux to pressure driven flow should be greater than 100:1. Depending upon the nature of the barrier the desirable pressure difference may be as low as 0.01 to 0.1 Pa.

BRIEF SUMMARY

A measurement apparatus is disclosed in which a barrier separates a chamber into a first region and a second region. The barrier is of a known thickness (T), and it comprises holes having a known radius (R). Gas flow means provide a flow of a carbon dioxide in the first region and a flow of a nitrogen in the second region. A gas detector measures the concentration of carbon dioxide in the second region and a processor calculates the theoretical diffusive flux from one region to another based on the known properties of the through-holes. The processor is arranged to calculate a calibration parameter in order to relate the measured parameter to the theoretical diffusive flux, based on the known properties of the through-holes.

One object of the present disclosure is to describe an improved measurement apparatus for measuring the diffusion capacity of a barrier or the diffusive flux through a barrier and a method for calibrating the apparatus.

DETAILED DESCRIPTION

Figure 1:
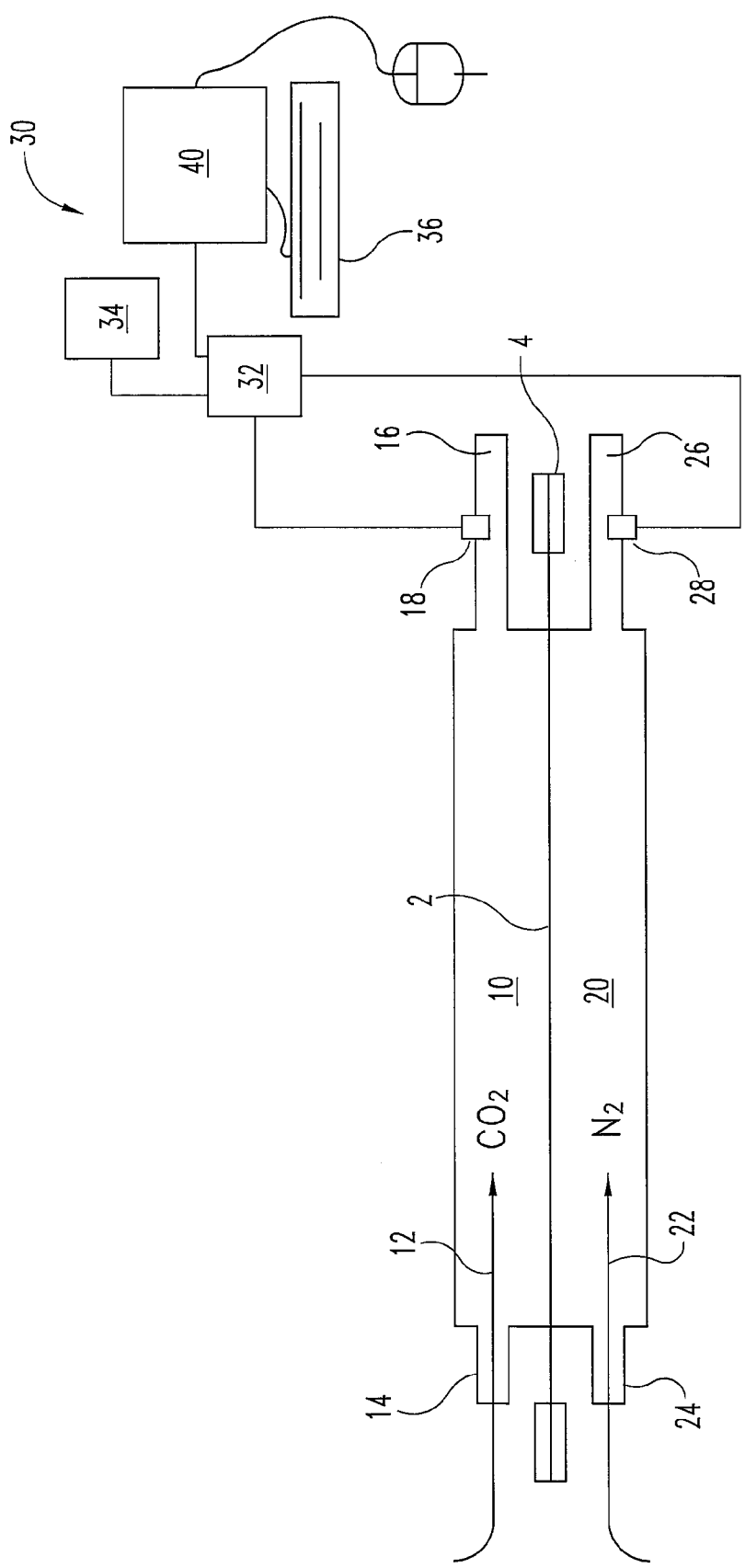
FIG. 1 shows a cross-sectional view of a measurement apparatus arranged in a calibration set-up, in an embodiment of the present invention.

For the purposes of promoting an understanding of the disclosure, reference will now be made to the embodiments illustrated in the drawings and specific language will be used to describe the same. It will nevertheless be understood that no limitation of the scope of the disclosure is thereby intended, such alterations and further modifications in the illustrated device and its use, and such further applications of the principles of the disclosure as illustrated therein being contemplated as would normally occur to one skilled in the art to which the disclosure relates.

FIG. 1 shows a measurement apparatus arranged in a calibration set-up. The apparatus comprises a barrier 2 clamped at its periphery by clamps 4. The barrier 2 separates a chamber into a first region 10 and a second region 20. Gas flow means are provided (not shown) to provide a flow of a carbon dioxide 12 in the first region 10 and the flow of a nitrogen 22 in the second region 20. Of course, any other gases may be used instead of carbon dioxide and nitrogen, and the first and second gases could even include different relative concentrations of the same gases.

The carbon dioxide and nitrogen 12, 22 enter the first and second regions 10, 20 via inlet ports 14, 24. Exit ports 16, 26 are provided to exhaust the gases 12, 22. Generally, the carbon dioxide and nitrogen 12, 22 are provided with mass flows such that there is no pressure differential across the barrier 2 which depends upon the downstream pressure drop to atmosphere of the two paths.

The first and second regions 10, 20 comprise respective gas $CO_2$ detectors 18, 28. In this way, the gas detectors 18, 28 can detect the degree to which gases have diffused across the barrier 2 from the opposite region.

The gas detectors 18, 28 are connected to a computer 30 comprising a processor 32 and a data storage unit 34. The computer 30 also comprises a keyboard 36, a mouse 38, and a visual display unit 40.

Figure 2:
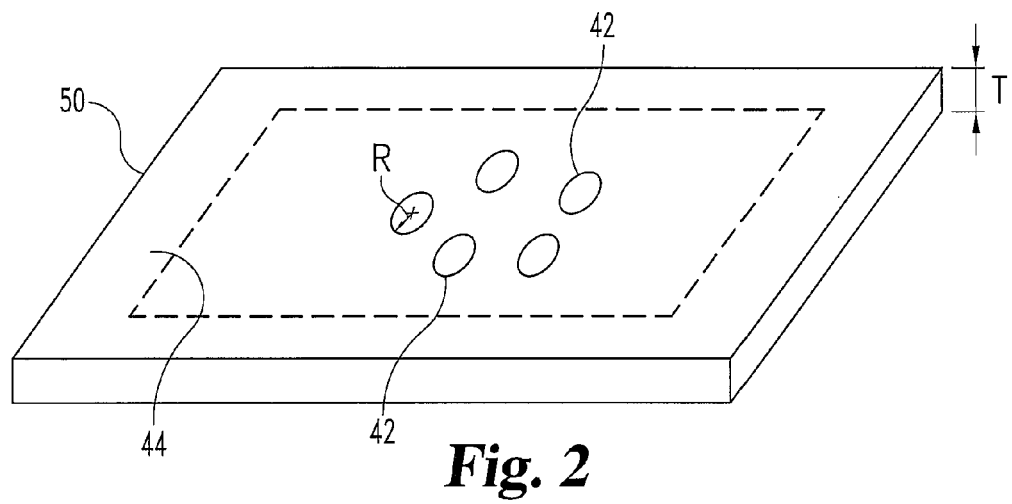
FIG. 2 shows a perspective view of a first embodiment of a calibration barrier for use in calibrating measurement apparatus in an embodiment of the invention.

FIG. 2 shows a perspective view of a barrier 50 which may be used in the apparatus of FIG. 1. The barrier 50 is made of metal foil and it comprises a number of holes 42. The barrier is arranged to be clamped by clamps 4 around its periphery 44, as can be seen in FIG. 2.

The barrier 50 is of a known thickness T, and the radius R of each hole is known. The thickness T and the radius R of each hole can be determined by optical inspection, or by any other convenient means. The holes 42 can be created in the barrier 50 by laser drilling or by any other appropriate means.

When clamped in the measurement apparatus, any diffusion through the barrier 50 occurs because of diffusion through the holes 42. The metal foil is impermeable to gases, and therefore diffusion through the fabric of the material is not possible except through the holes 42.

In use, the barrier 50 is clamped in the clamps 4, a flow of carbon dioxide is applied to the first region 10, and a flow of nitrogen 22 is applied to the second region 20. The gas detector 28 measures the concentration of $CO_2$ once a steady-state has been achieved (typically in a few seconds). The concentration of $CO_2$ measured by the gas detector 28 will be higher when the diffusion capacity of the barrier 50 is high, and lower when the diffusion capacity of the barrier 50 is low. The gas detector 28 communicates the measurement of concentration of $CO_2$ to the processor 32 in the computer 30.

The measurement of the concentration of $CO_2$ by the gas detector 28 can be converted into a measured diffusive flux of $CO_2$ across the barrier 50 from the first region 10 to the second region 20. This measured diffusive flux is likely to be inaccurate because of numerous environmental influences and drift in equipment. Thus, calibration of the apparatus is required.

A user enters the properties of the through-holes in the barrier 50 into the computer 30 via the keyboard 36. The processor 32 is then able to calculate the theoretical diffusive flux of $CO_2$ across the barrier 50 so that this can be compared with the diffusive flux measured by the gas detector 28.

The theoretical diffusive flux is calculated according to the expression:

$$J = \frac{D\pi\Delta C \sum_i R^2}{T} \quad (1)$$

Where:

J is the measured flux of the diffusing species across the barrier in $m^2 \, s^{-1}$;

D is the known diffusivity of the analysed gas in the holes formed in the barrier measured in $m^2 \, s^{-1}$. This represents the propensity of carbon dioxide and nitrogen to diffuse with one another;

$\Delta C$ is the difference in concentration of the diffusing species on either side of the barrier;

T is the thickness of each hole;

R is the radius of each hole;

and the summation is performed over i holes.

The theoretical diffusion capacity of the barrier can then be determined with the expression:

$$D^* = \frac{J}{A} \quad (2)$$

Where:

$D^*$ is the diffusion capacity of the barrier in $ms^{-1}$;

A is the area enclosed by the clamp in $m^2$.

Thus, by accurately determining the radius R and the thickness T of each hole, it is possible to determine the theoretical diffusion flux of $CO_2$ across the barrier 50 in a given set of experimental conditions. This may, of course, be converted into the theoretical $CO_2$ concentration level that would be expected for detection by the gas detector 28.

The processor 32 is arranged to calculate an appropriate calibration parameter in order to relate the calculated theoretical diffusive flux with the measured diffusive flux. The calibration parameter calculated by the processor 32 is then stored in the data storage unit 34.

In this way, the barrier 50 can be used to calibrate the measurement apparatus. The computer 30 may be arranged in a calibration mode so that this process can occur. In the calibration mode, for example, the processor 32 may prompt the user to enter the known properties of the through-holes in the barrier 50 via the keyboard 36.

Once a calibration parameter has been calculated and stored, the barrier 50 can be removed from the clamps 4 of the apparatus, and a new sample barrier can be inserted. The sample barrier may be, for example, cigarette wrapping paper for use in fire safe standard compliant smoking articles.

The diffusion capacity of the new sample barrier can then be determined with the computer 30 arranged in a measurement mode. The first step is to measure the concentration of $CO_2$ at gas detector 28 in the steady-state in order to determine a measured diffusive flux through the barrier. The second step is to determine a calibrated diffusive flux with the processor 32 making use of the calibration parameter stored in the data storage unit 34. The diffusion capacity of the barrier can then be determined by the processor 32 using expression (2). The calibrated diffusive flux or the calibrated diffusion capacity of the sample barrier calculated by the processor 32 is then displayed on the visual display unit 40. Thus, in the measurement mode the computer 30 may display the calculated diffusivity on the visual display unit 40 without prompting the user to enter any details.

In this example the processor 32 is arranged to calculate an appropriate calibration parameter in order to relate the calculated theoretical diffusive flux with the measured diffusive flux. In an alternative example equation (1) could be re-arranged so that the expected properties of the through-holes are calculated from the measured flux of the diffusing species across the barrier, J. The calibration parameter may then be used to relate the known properties of the through-holes with the expected properties, based on the measured parameter J. In both examples the calibration parameter relates a parameter derived from a measured quantity and a parameter derived from a known quantity, based on the properties of the through-holes.

Figure 3:
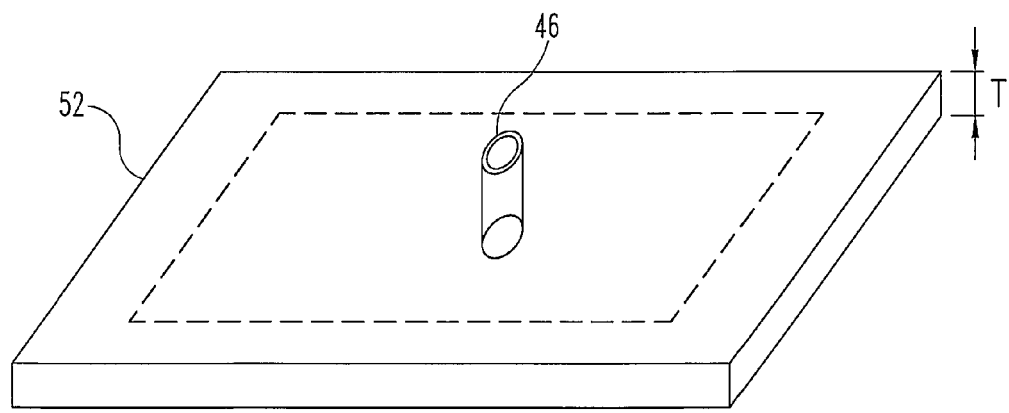
FIG. 3 shows a perspective view of a second embodiment of a calibration barrier for use in calibrating measurement apparatus in an embodiment of the invention.

FIG. 3 shows a perspective view of an alternative embodiment of a barrier 52 for use in calibrating the measurement apparatus. The barrier 52 comprises a capillary tube 46 that is fixed to the metal foil and extends from a planar surface thereof. The capillary tube 46 is made of glass or ceramic material and it is cylindrical. The depth of the hole T defined by the capillary tube 46 is equal to the length of the tube plus the thickness of the foil. An advantage of using a capillary tube 46 is that it can be manufactured to have known properties; in particular, it can be a regular cylinder with well defined edges. Thus, the flow of gases through the tube 46 may occur in a more predictable way than the flow of gases through a laser-drilled hole which may be non-cylindrical and may have ragged edges. Accordingly, the theoretical diffusive flux through the barrier 52, calculated according to equation (1), may be more accurate for a barrier comprising capillary tubes.

While the preferred embodiment of the invention has been illustrated and described in the drawings and foregoing description, the same is to be considered as illustrative and not restrictive in character, it being understood that all changes and modifications that come within the spirit of the invention are desired to be protected.

The invention claimed is:

1. Measurement apparatus comprising:

a chamber;

a barrier separating the chamber into first and second regions, wherein the barrier comprises one or more through-holes each with known properties, and wherein the barrier is of a material that is substantially impermeable to air in the absence of any through-holes;

a detector arranged to measure a parameter that is related to the diffusive flux of a gas from one region to the other, through the barrier;

a processor arranged to calculate a calibration parameter, wherein the calibration parameter can be applied to link a first parameter derived from the measurement by the detector and a second parameter that is derived independently of the measurement by the detector and is related to a theoretical diffusive flux through the barrier, based on the known properties of the through-holes; and data storage means for storing the calibration parameter calculated by the processor, wherein the barrier is replaceable by a further barrier, such that the apparatus is able to determine a calibrated diffusive flux across the further barrier by measuring a parameter with the detector and applying the calibration parameter stored in the data storage means.

2. The measurement apparatus of claim 1, wherein said known properties of the through-holes include the depth and area of the through-holes.

3. The measurement apparatus of claim 1, wherein at least one of the through-holes in the barrier has a depth that is greater than the thickness of the barrier.

4. The measurement apparatus of claim 3, wherein the at least one through-hole with a depth that is greater than the thickness of the barrier is defined at least in part by a tube that is fixed to the barrier.

5. The measurement apparatus of claim 1, wherein at least one of the through-holes in the barrier has a depth equal to the thickness of the barrier.

6. The measurement apparatus of claim 1, wherein the detector is provided in the first region and the detector is arranged to measure the concentration of a gas in the first region, at least some of the gas having diffused into the first region from the second region, through the barrier.

7. The measurement apparatus of claim 6, comprising a further detector provided in the second region, and arranged to measure the concentration of a gas in the second region at least in part due to the diffusion of the gas from the first region, through the barrier.

8. The measurement apparatus of claim 1, wherein the barrier is made of one of metal, glass, ceramic and/or polymer material.

9. A method of determining a calibrated diffusive flux of gas through paper for a smoking article, the method comprising the steps of:
    separating a chamber into first and second regions with a barrier, wherein the barrier comprises one or more through-holes each with known properties, and wherein the barrier is of a material that is substantially impermeable to air in the absence of any through-holes,
    using a detector to measure a parameter that is related to the diffusive flux of gas from one region to the other, through the barrier;
    using a processor to calculate a calibration parameter, wherein the calibration parameter can be applied to link a first parameter derived from the measurement and a second parameter that is derived independently of the measurement by the detector and is related to a theoretical diffusive flux through the barrier, based on the known properties of the through-holes; and
    using data storage means to record the calibration parameter;
    replacing the barrier with a paper for a smoking article to separate the chamber into first and second regions;
    using the detector to measure a parameter that is related to the diffusive flux of gas from one region to the other, through the paper; and
    using the processor to calculate a calibrated diffusive flux at least in part by applying the recorded calibration parameter to the measured parameter.

10. The method of claim 9, further comprising the step of using the processor to calculate a parameter that is related to the theoretical diffusive flux through the barrier, wherein the calculation is based on the known properties of the through-holes, and wherein the calculated calibration parameter connects the calculated parameter and the measured parameter.

11. The method of claim 9, wherein said known properties of the through-holes include the depth and area of the through-holes.

12. The method of claim 9, wherein the step of measuring the parameter involves using the detector to measure a concentration of a gas in the first region of the chamber at least in part due to the diffusion of the gas from the second region of the chamber, through the barrier.

13. A method according to claim 9, wherein the paper is fire standard compliant cigarette paper.

* * * * *